(12) United States Patent
Sano

(10) Patent No.: US 8,878,142 B2
(45) Date of Patent: Nov. 4, 2014

(54) CHARGED PARTICLE BEAM IRRADIATION APPARATUS

(71) Applicant: Sumitomo Heavy Industries, Ltd., Tokyo (JP)

(72) Inventor: Masami Sano, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/063,755

(22) Filed: Oct. 25, 2013

(65) Prior Publication Data
US 2014/0048718 A1 Feb. 20, 2014

(30) Foreign Application Priority Data
Apr. 25, 2011 (JP) ................. 2011-097297

(51) Int. Cl.
*G21K 5/10* (2006.01)
*A61N 5/10* (2006.01)
*G21K 5/04* (2006.01)

(52) U.S. Cl.
CPC ................ *A61N 5/1081* (2013.01); *G21K 5/10* (2013.01); *A61N 2005/1087* (2013.01); *G21K 5/04* (2013.01)
USPC ................ 250/396 R; 250/398; 250/396 ML; 250/492.1; 250/492.3; 250/505.1

(58) Field of Classification Search
CPC ........... G21K 5/04; G21K 5/10; G21K 1/093; G21K 1/08; A61N 2005/1087; A61N 5/1081; A61N 5/1042; A61N 2005/1094
USPC ........ 250/396 R, 398, 396 ML, 492.1, 492.3, 250/505.1
See application file for complete search history.

(56) References Cited

U.S. PATENT DOCUMENTS

| | | | | |
|---|---|---|---|---|
| 4,917,344 | A | * | 4/1990 | Prechter et al. ............... 248/664 |
| 5,039,057 | A | | 8/1991 | Prechter et al. |
| 5,818,058 | A | * | 10/1998 | Nakanishi et al. ......... 250/492.3 |
| 5,993,373 | A | * | 11/1999 | Nonaka et al. .................... 600/1 |
| 6,316,776 | B1 | * | 11/2001 | Hiramoto et al. ......... 250/492.3 |
| 6,670,618 | B1 | * | 12/2003 | Hartmann et al. ......... 250/491.1 |
| 6,683,318 | B1 | * | 1/2004 | Haberer et al. ............ 250/492.3 |
| 7,030,396 | B2 | * | 4/2006 | Muramatsu et al. ....... 250/492.3 |
| 7,372,053 | B2 | * | 5/2008 | Yamashita et al. ......... 250/492.3 |
| 8,653,473 | B2 | * | 2/2014 | Yajima ...................... 250/396 R |

(Continued)

*Primary Examiner* — Michael Logie
(74) *Attorney, Agent, or Firm* — Rader, Fishman & Grauer PLLC

(57) ABSTRACT

A charged particle beam irradiation apparatus includes: a transport line configured to transport a charged particle beam; and a rotating gantry rotatable around a rotation axis, wherein the transport line has an inclined section configured to make the charged particle beam advancing in a direction of the rotation axis advance to be inclined so as to become more distant from the rotation axis, and is formed so as to turn the charged particle beam advanced in the inclined section to a rotational direction of the rotation axis and bend the charged particle beam turned to the rotational direction to the rotation axis side, the rotating gantry is formed of a tubular body which can accommodate an irradiated body and supports the transport line, and the inclined section is disposed to pass through the inside of the tubular body of the rotating gantry.

3 Claims, 8 Drawing Sheets

(56) References Cited

U.S. PATENT DOCUMENTS

| | | | |
|---|---|---|---|
| 8,664,620 B2 * | 3/2014 | Haruna et al. | 250/396 R |
| 2004/0183034 A1 * | 9/2004 | Yanagisawa et al. | 250/492.3 |
| 2005/0063516 A1 * | 3/2005 | Kato et al. | 378/152 |
| 2010/0163755 A1 * | 7/2010 | Takeda et al. | 250/492.3 |
| 2011/0299657 A1 * | 12/2011 | Havelange et al. | 378/65 |
| 2012/0280150 A1 * | 11/2012 | Jongen | 250/492.3 |
| 2013/0289330 A1 * | 10/2013 | Haruna et al. | 600/1 |
| 2014/0058186 A1 * | 2/2014 | Sasai | 600/1 |

\* cited by examiner

CHARGED PARTICLE BEAM IRRADIATION APPARATUS

INCORPORATION BY REFERENCE

Priority is claimed to Japanese Patent Application No. 2011-097297, filed Apr. 25, 2011, and International Patent Application No. PCT/JP2012/055852, the entire content of each of which is incorporated herein by reference.

BACKGROUND

1. Technical Field

The present invention relates to a charged particle beam irradiation apparatus that irradiates a charged particle beam.

2. Description of the Related Art

Equipment which performs cancer therapy by irradiating a patient with a charged particle beam such as proton beam is known. This type of equipment is provided with a cyclotron (an accelerator) which accelerates charged particles and emits a charged particle beam, a rotating gantry (a rotating body) on which a rotatable irradiation section which irradiates the patient with the charged particle beam from an arbitrary direction is mounted, and a transport line which transports the charged particle beam emitted from the cyclotron to the irradiation section.

The irradiation section is configured so as to be rotatable with respect to the patient, and various forms of the transport line which transports the charged particle beam to the irradiation section are known. For example, a beam transport line mounted on a rotating gantry described in the related art is disposed so as to make the charged particle beam advancing in a direction of a rotation axis of the rotating gantry advance to be inclined so as to become more distant from the rotation axis, thereafter, turn the charged particle beam to a rotational direction of the rotation axis and then make the charged particle beam advance by a predetermined distance, and bend the charged particle beam advanced by the predetermined distance to the rotation axis side and then transport the charged particle beam to the irradiation section (a nozzle 32). Furthermore, the beam transport line disposed in this manner is supported by a truss-like structure (the rotating gantry).

SUMMARY

According to an embodiment of the present invention, there is provided a charged particle beam irradiation apparatus including: a transport line configured to transport a charged particle beam; and a rotating gantry rotatable around a predetermined rotation axis, wherein the transport line has an inclined section configured to make the charged particle beam advancing in a direction of the rotation axis advance to be inclined so as to become more distant from the rotation axis, and is formed so as to turn the charged particle beam advanced in the inclined section to a rotational direction of the rotation axis and bend the charged particle beam turned to the rotational direction to the rotation axis side, the rotating gantry is formed of a tubular body which can accommodate an irradiated body and supports the transport line, and the inclined section of the transport line is disposed to pass through the inside of the tubular body of the rotating gantry.

According to another embodiment of the present invention, there is provided a charged particle beam irradiation apparatus including: a transport line configured to transport a charged particle beam; and a rotating gantry rotatable around a predetermined rotation axis, wherein the transport line has at least an inclined section configured to make the charged particle beam advancing in a direction of the rotation axis advance to be inclined so as to become more distant from the rotation axis, the rotating gantry has an irradiation chamber of a tubular body in which one end side in a direction in which the rotation axis extends is closed by a back panel, and the inclined section of the transport line is disposed to pass through the back panel and the inside of the tubular body of the rotating gantry.

DETAILED DESCRIPTION

Figure 1:
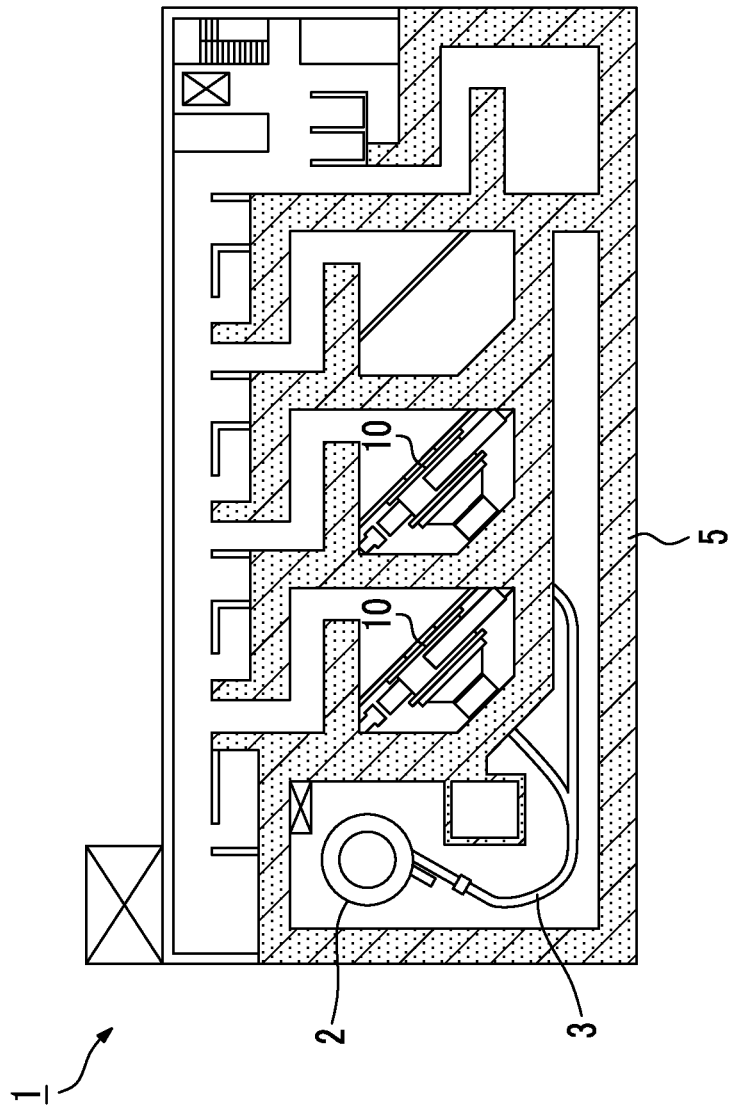
FIG. 1 is a schematic configuration diagram of a proton beam therapy system provided with a proton beam therapy apparatus according to an embodiment of the present invention.

In a beam transport line described in the related art, a length in the direction of a rotation axis is shortened, and thus a reduction in size is attained. However, the size in a radial direction that is a direction crossing the rotation axis is greatly increased. Furthermore, since an electromagnet and the like forming the beam transport line are supported by the truss-like structure formed so as to overhang outward in the radial direction, the entire rotating gantry device is greatly increased in size in the radial direction. For this reason, an accommodation space which accommodates the rotating gantry also becomes wide, thereby leading to an increase in the size of a building in which the rotating gantry is installed, and thus it is difficult to reduce construction cost.

It is desirable to attain a reduction in the size of a charged particle beam irradiation apparatus.

The charged particle beam irradiation apparatus according to the embodiment of the present invention is provided with the rotating gantry having a tubular body rotatable around the rotation axis, and a portion of the transport line which transports the charged particle beam is formed so as to pass through the inside of the tubular body of the rotating gantry. As a portion of the transport line, the inclined section which makes the charged particle beam advancing in the direction of the rotation axis advance to be inclined so as to become more distant from the rotation axis is disposed so as to pass through the inside of the tubular body. In this manner, if the inclined section of the transport line, which becomes more distant in the radial direction from the rotation axis, is disposed so as to pass through the inside of the tubular body of the rotating gantry, as compared with a case where the transport line is disposed to avoid the inside of the tubular body (for example, enclosure or irradiation chamber), it is possible to suppress the amount of overhanging of the transport line in the radial direction, and thus it is possible to reduce the size of the entire apparatus in the radial direction. Accordingly, a space for accommodating the charged particle beam irradiation apparatus is reduced, and thus it is possible to attain a reduction in the size of a building. By reducing the size of the building, it is possible to reduce the amount of concrete which is used for, for example, a radiation shield wall, and therefore, it is possible to reduce the construction cost of the building.

Furthermore, as a specific configuration of the transport line, a configuration can be given in which the transport line is provided with a first bent section configured to change a traveling direction of the charged particle beam advancing in the direction of the rotation axis and introduce the charged particle beam into the inclined section, a second bent section which is provided downstream of the inclined section and configured to change the traveling direction of the charged particle beam to a direction orthogonal to the rotation axis, a third bent section which is provided downstream of the second bent section and configured to change the traveling direction of the charged particle beam to a rotational direction of the rotation axis, and a fourth bent section configured to bend the charged particle beam passed through the inside of the third bent section to the rotation axis side. Through the transport line configured in this manner, overhanging in the radial direction of the transport line is suppressed, and thus a reduction in the size of the charged particle beam apparatus can be attained.

The charged particle beam irradiation apparatus according to the embodiment of the present invention may be provided with the rotating gantry having a tubular body rotatable around the rotation axis. The rotating gantry may be configured to have an irradiation chamber that is a tubular body in which one end side in a direction in which the rotation axis extends is closed by a back panel. A portion of the transport line which transports the charged particle beam may be formed so as to pass through the back panel and the inside of the tubular body of the rotating gantry. As a portion of the transport line, the inclined section which makes the charged particle beam advancing in the direction of the rotation axis advance to be inclined so as to become more distant from the rotation axis may be disposed so as to pass through the back panel and the inside of the tubular body.

In this manner, if the inclined section of the transport line which becomes more distant in the radial direction from the rotation axis is disposed so as to pass through the back panel and the inside of the tubular body of the rotating gantry, as compared with a case where the transport line is disposed to avoid the back panel and the inside of the tubular body (for example, an enclosure or an irradiation chamber), it is possible to suppress the amount of overhanging of the transport line in the radial direction, and thus it is possible to reduce the size of the entire apparatus in the radial direction. Accordingly, a space for accommodating the charged particle beam irradiation apparatus is reduced, and thus it is possible to attain a reduction in the size of the building. By reducing the size of the building, it is possible to reduce the amount of concrete which is used for, for example, a radiation shield wall, and therefore, it is possible to reduce the construction cost of the building.

According to the embodiments of the present invention, it is possible to attain a reduction in the size of the charged particle beam irradiation apparatus, thereby reducing an apparatus accommodation space and thus attaining a reduction in the size of the building. Accordingly, it is effective for a reduction in the construction cost of the building in which the charged particle beam irradiation apparatus is installed.

Hereinafter, a preferred embodiment of a charged particle beam irradiation apparatus according to the present invention will be described referring to the drawings. In this embodiment, a proton beam therapy system provided with a proton beam therapy apparatus (a charged particle beam irradiation apparatus) will be described. The proton beam therapy apparatus is applied to, for example, cancer therapy and is an apparatus for irradiating a proton beam (a charged particle beam) with respect to a tumor (an irradiated body) in the body of a patient.

As shown in FIG. 1, a proton beam therapy system 1 has a cyclotron (a particle accelerator) 2 which generates a proton beam, a beam transport line 3 which transports the proton beam emitted from the cyclotron 2, and a proton beam therapy apparatus 10 which irradiates the irradiated body with the proton beam transported by the beam transport line 3. Then, each of apparatuses of the proton beam therapy system 1 is accommodated in a building 5.

The pathway of the proton beam accelerated by the cyclotron 2 is deflected along the beam transport line 3 and supplied to the proton beam therapy apparatus 10. A deflection magnet for deflecting the pathway of the proton beam, a quadrupole electromagnet which performs beam shaping, or the like, is provided in the beam transport line 3.

The proton beam therapy apparatus 10 is provided with a beam introduction line 31 which transports the proton beam that is introduced by the beam transport line 3, a beam irradiation nozzle 11 which irradiates the irradiated body with the proton beam transported by the beam introduction line 31, and a rotating gantry 12 which supports the beam introduction line 31 and the beam irradiation nozzle 11 and can rotate around a predetermined rotation axis P, as shown in FIGS. 2 to 8.

Figure 7:
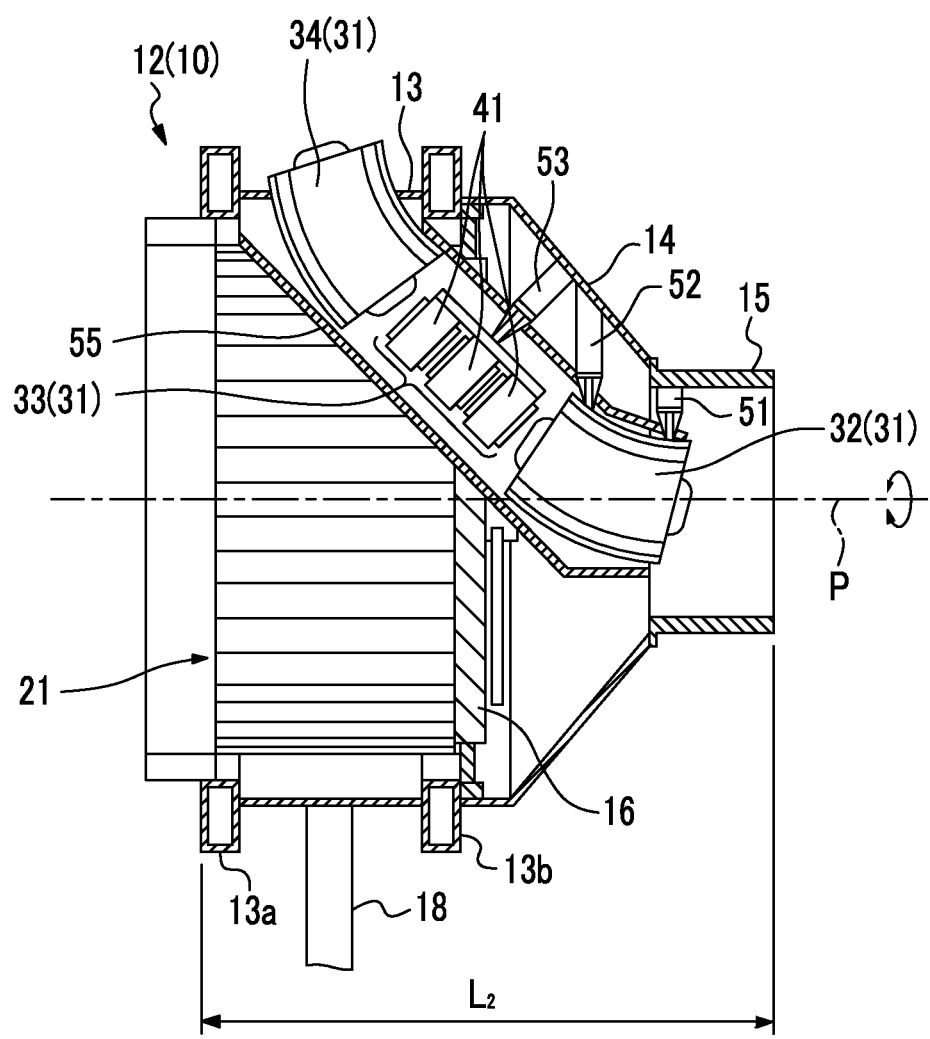
FIG. 7 is a schematic cross-sectional view of a rotating gantry of the proton beam therapy apparatus according to the embodiment of the present invention which is cut in a horizontal direction along a rotation axis.

The rotating gantry 12 has a cylindrical main body section 13, a cone section 14, and a second cylindrical section 15 which are disposed in order in a direction of the rotation axis P, as shown in FIG. 7. The cylindrical main body section 13, the cone section 14, and the second cylindrical section 15 are disposed on the same axis (the rotation axis P) and are connected to each other. In addition, the side where the cylindrical main body section 13 is disposed is set as the front side of the rotating gantry 12 and the side where the second cylindrical section 15 is disposed is set as the back side of the rotating gantry 12.

Each of the cylindrical main body section 13 and the second cylindrical section 15 is a cylindrical body having a thin-walled structure and is configured so as to be able to reduce weight while maintaining rigidity. The second cylindrical section 15 has a smaller diameter than that of the cylindrical main body section 13, and the cone section 14 is formed into a conical shape so as to connect the cylindrical main body section 13 and the second cylindrical section 15. The cone section 14 is a tubular body having a thin-walled structure and is formed such that an inner diameter is reduced going from the front side to the back side. Furthermore, the length of the rotating gantry 12 in the direction of the rotation axis P (the length from an end portion on the front side of the cylindrical main body section 13 to an end portion on the back side of the second cylindrical section 15) is made to be, for example, $L_2$=about 4.6 m.

Ring sections 13a and 13b, the cross-sectional shapes of which are, for example, rectangular, are provided at both end portions of the cylindrical main body section 13 in the direction of the rotation axis P. The cylindrical main body section 13 is rotatably supported by a roller device 20 disposed below the cylindrical main body section 13, as shown in FIGS. 2 to 5. The roller device 20 functions as a driving device for rotating the rotating gantry 12.

The front side of the cylindrical main body section 13 is opened, and thus a configuration is made in which entry into the cylindrical main body section 13 is possible. On the other hand, a back panel (a partition wall) 16 is provided on the back side of the cylindrical main body section 13. Then, an irradiation chamber 21 is configured by the cylindrical main body section 13 and the back panel 16. A bed (a treatment table) 22 on which a patient lies down can be disposed in the irradiation chamber 21. The bed 22 can be moved by a robot arm 23. During normal time when therapy is not carried out, the bed 22 is disposed outside the rotating gantry 12 (the irradiation chamber 21), and when carrying out the therapy, the bed 22 is disposed in the irradiation chamber 21. In addition, in FIG. 7, illustration of the bed 22 is omitted.

The irradiation nozzle 11 is fixed to the inner surface side of the cylindrical main body section 13 and rotates around the rotation axis P along with the cylindrical main body section 13. The irradiation nozzle 11 moves with the rotation of the cylindrical main body section 13, and thus an emission direction of the proton beam is changed.

The beam introduction line 31 that is a beam transport line of the proton beam therapy apparatus 10 is connected to the beam transport line 3 which transports the proton beam emitted from the cyclotron 2, and introduces the proton beam transported by the beam transport line 3 into the irradiation nozzle 11.

Figure 8:
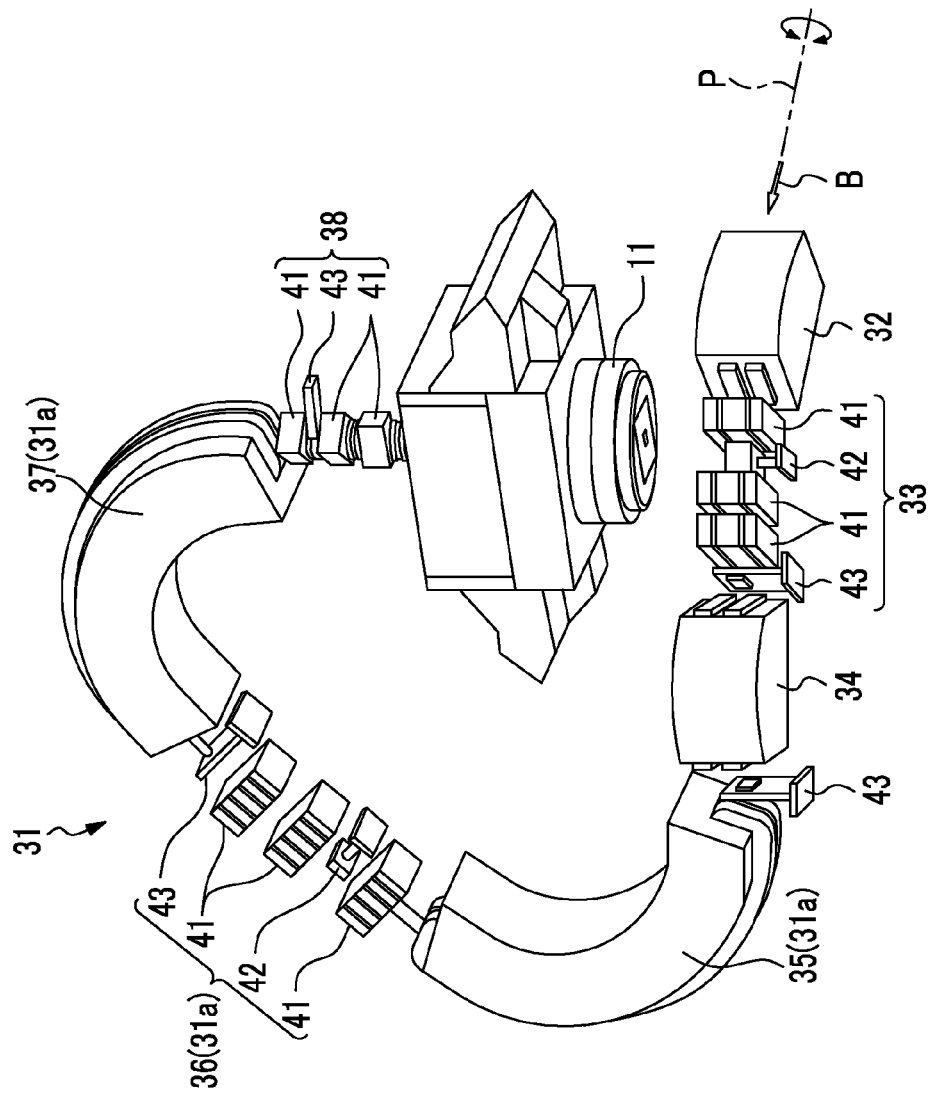
FIG. 8 is a perspective view showing a beam transport line and a beam irradiation nozzle mounted on the rotating gantry.

FIG. 8 is a perspective view showing the beam introduction line and the beam irradiation nozzle mounted on the rotating gantry. The beam introduction line 31 is provided with a first bent section 32 which deflects a traveling direction of the proton beam advancing in the direction of the rotation axis P of the rotating gantry 12, an inclined section 33 which is provided downstream of the first bent section 32 and makes a proton beam B advance to be inclined with respect to the direction of the rotation axis P, a second bent section 34 which is provided downstream of the inclined section 33 and deflects the traveling direction of the proton beam B in a direction orthogonal to the rotation axis P, a third bent section 35 which is provided downstream of the second bent section 34 and turns the traveling direction of the proton beam B to a rotational direction of the rotation axis P, a linear section 36 which is provided downstream of the third bent section 35 and makes the proton beam B advance to the upper side (an upper side in the state shown in FIG. 2) of the irradiation nozzle 11, a fourth bent section 37 which is provided downstream of the linear section 36 and bends the proton beam B to the axis center side (the rotation axis P side), and a linear section 38 which is provided downstream of the fourth bent section 37 and makes the proton beam B advance to the irradiation nozzle 11.

The first bent section 32 is configured to have a 45-degree deflection electromagnet which bends the proton beam B so as to deflect the traveling direction by 45 degrees. The inclined section 33 is configured to have optical elements such as a quadrupole electromagnet 41, a steering electromagnet 42, and a profile monitor 43. The quadrupole electromagnet 41 has a function of adjusting the size at an irradiation position of the proton beam B or an optical focus position. The steering electromagnet 42 has a function of parallel-shifting a beam axis. The profile monitor 43 has a function of detecting the shape and the position of the proton beam B which passes therethrough.

The second bent section 34 is configured to have a 45-degree deflection electromagnet which bends the proton beam B so as to deflect the traveling direction by 45 degrees. Furthermore, the profile monitor 43 is disposed between the second bent section 34 and the third bent section 35. The third bent section 35 is configured to have a 135-degree deflection electromagnet which bends the proton beam B so as to deflect the traveling direction by 135 degrees.

The linear section 36 has the quadrupole electromagnet 41, the steering electromagnet 42, and the profile monitor 43. The fourth bent section 37 is configured to have a 135-degree deflection electromagnet which bends the proton beam B so as to deflect the traveling direction by 135 degrees. The linear section 38 has the quadrupole electromagnet 41 and the profile monitor 43.

Here, in the proton beam therapy apparatus 10 according to this embodiment, a portion of the beam introduction line 31 mounted on the rotating gantry 12 is disposed to pass through the insides of tubular bodies (the cylindrical main body section 13, the cone section 14, and the second cylindrical section 15) of the rotating gantry 12. The proton beam B transported by the beam transport line 3 is introduced into the inside from the back side of the second cylindrical section 15, passes through the inside of the second cylindrical section 15, the inside of the cone section 14, the back panel 16, and the inside of the cylindrical main body section 13, and penetrates the cylindrical main body section 13, thereby being led out of the cylindrical main body section 13.

The rotating gantry 12 is provided with first to third support members 51 to 53 which support the beam introduction line 31. The first bent section 32 is fixed to the second cylindrical section 15 by the first support member 51 and fixed to the cone section 14 by the second support member 52. The inclined section 33 is fixed to the cone section 14 by the third support member 53. The second bent section 34 penetrates the cylindrical main body section 13 and is supported by the cylindrical main body section 13.

The beam introduction line 31 is disposed so as to penetrate the back panel 16, enter the inside of the cylindrical main body section 13, and pass through the inside of the irradiation chamber 21. Furthermore, the rotating gantry 12 is provided with a casing 55 which accommodates the beam introduction line 31 that passes through the inside. The casing 55 is disposed along the beam introduction line 31 and covers the beam introduction line 31. The casing 55 is fixed to the cylindrical main body section 13, the cone section 14, and the second cylindrical section 15 through the first to third support members 51 to 53 or directly. Furthermore, it is preferable that the casing 55 be configured to have a shielding material (for example, polyethylene, lead, stainless steel, or the like) which shields a radiation such as a neutron radiation.

Furthermore, a stand 17 for supporting the beam introduction line 31 overhanging further outward than the cylindrical main body section 13 is provided on the outer peripheral surface of the cylindrical main body section 13. In addition, the beam introduction line 31 overhanging further outward than the cylindrical main body section 13 is referred to as a beam introduction line overhang portion 31a. The third bent section 35, the linear section 36, and the fourth bent section 37 are included in the beam introduction line overhang portion 31a. The stand 17 is fixed to the outer surface of the cylindrical main body section 13 and overhangs outward in a radial direction. The stand 17 supports the beam introduction line overhang portion 31a from the inside in the radial direction. In this way, load of electromagnets (the quadrupole electromagnet 41 and the 135-degree deflection electromagnet) or the like can be received by the cylindrical main body section 13.

Furthermore, a counterweight 18 disposed on the opposite side across the rotation axis P is provided on the outer peripheral surface of the cylindrical main body section 13. The counterweight 18 is installed, whereby weight balance against the third bent section 35, the linear section 36, the fourth bent section 37, and the stand 17 disposed on the outer surface of the cylindrical main body section 13 is secured.

Then, the rotating gantry 12 is rotationally driven by a motor (not shown) and the rotation thereof is stopped by a brake device (not shown).

In the proton beam therapy system 1, the proton beam B emitted from the cyclotron 2 is transported by the beam transport line 3 and reaches the proton beam therapy apparatus 10. The proton beam B which has reached the proton beam therapy apparatus 10 is transported by the beam introduction line 31, reaches the irradiation nozzle 11, and is irradiated to a tumor of a patient. The irradiation direction of the proton beam B which is irradiated from the irradiation nozzle 11 can be adjusted by rotating the rotating gantry 12.

Figure 2:
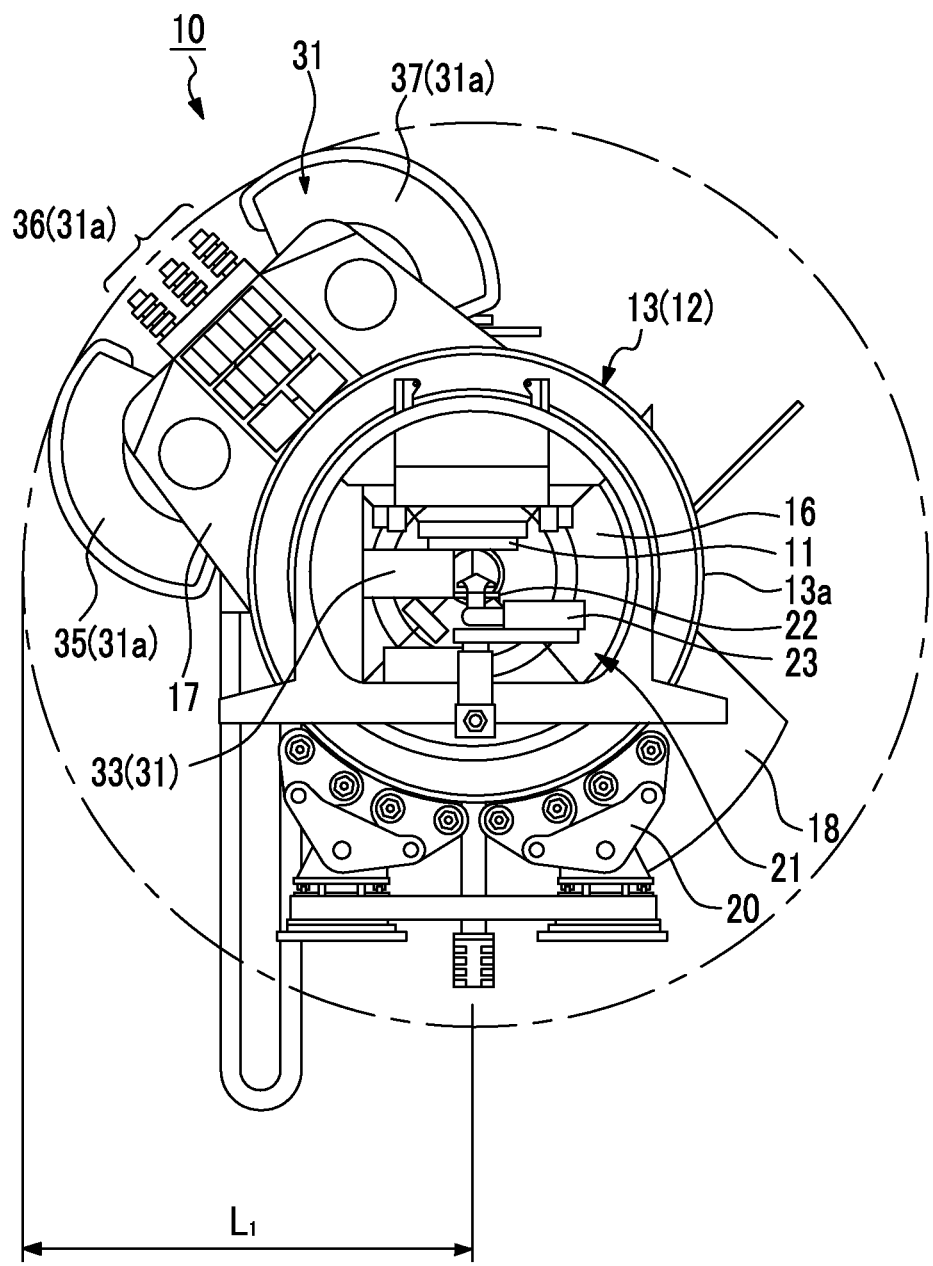
FIG. 2 is a front view of the proton beam therapy apparatus according to the embodiment of the present invention.
Figure 3:
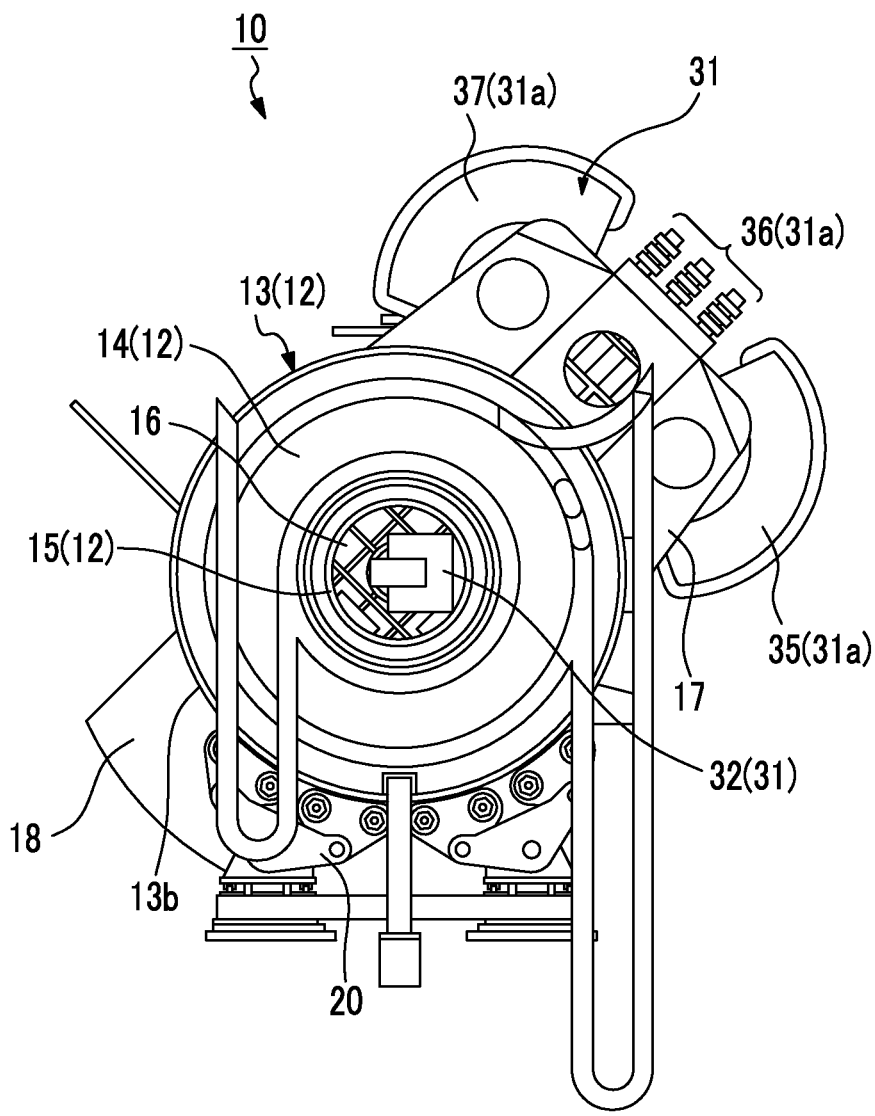
FIG. 3 is a back view of the proton beam therapy apparatus according to the embodiment of the present invention.
Figure 4:
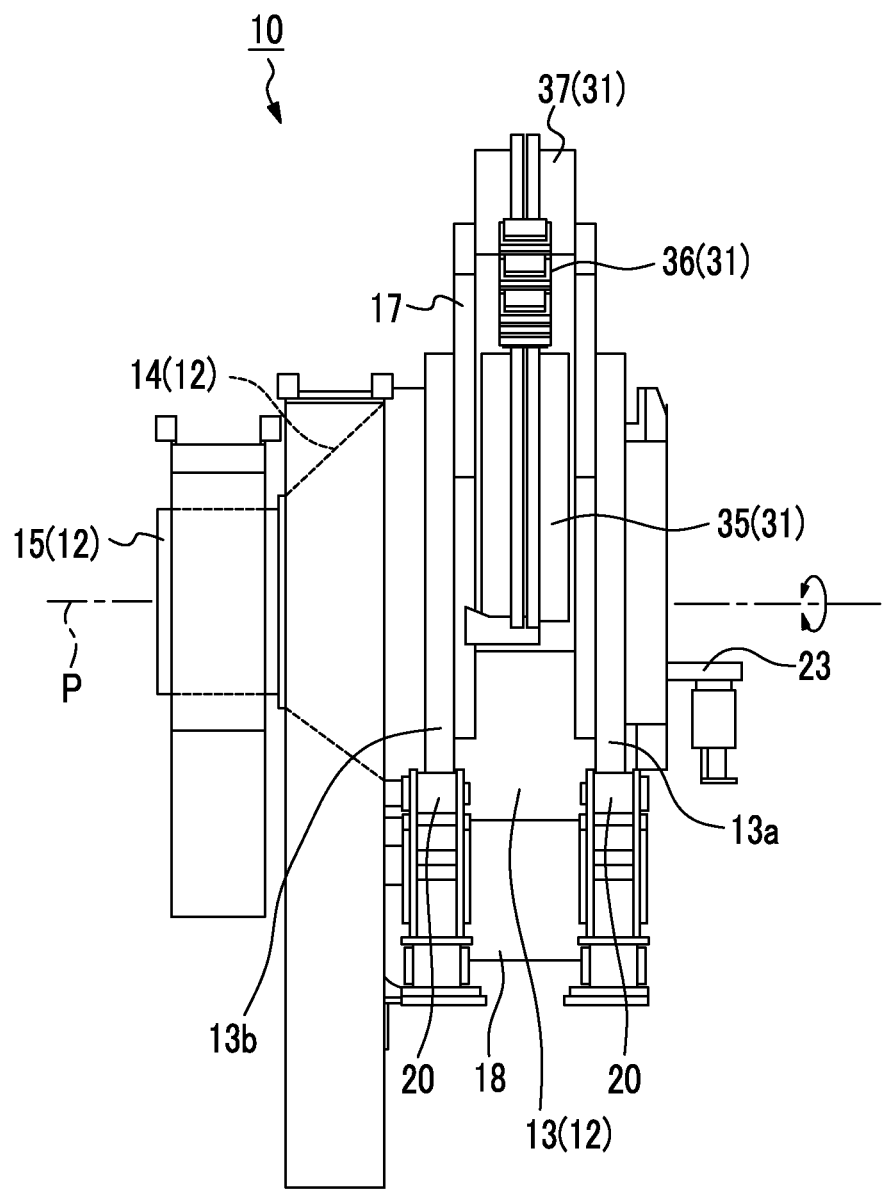
FIG. 4 is a right side view of the proton beam therapy apparatus according to the embodiment of the present invention.
Figure 5:
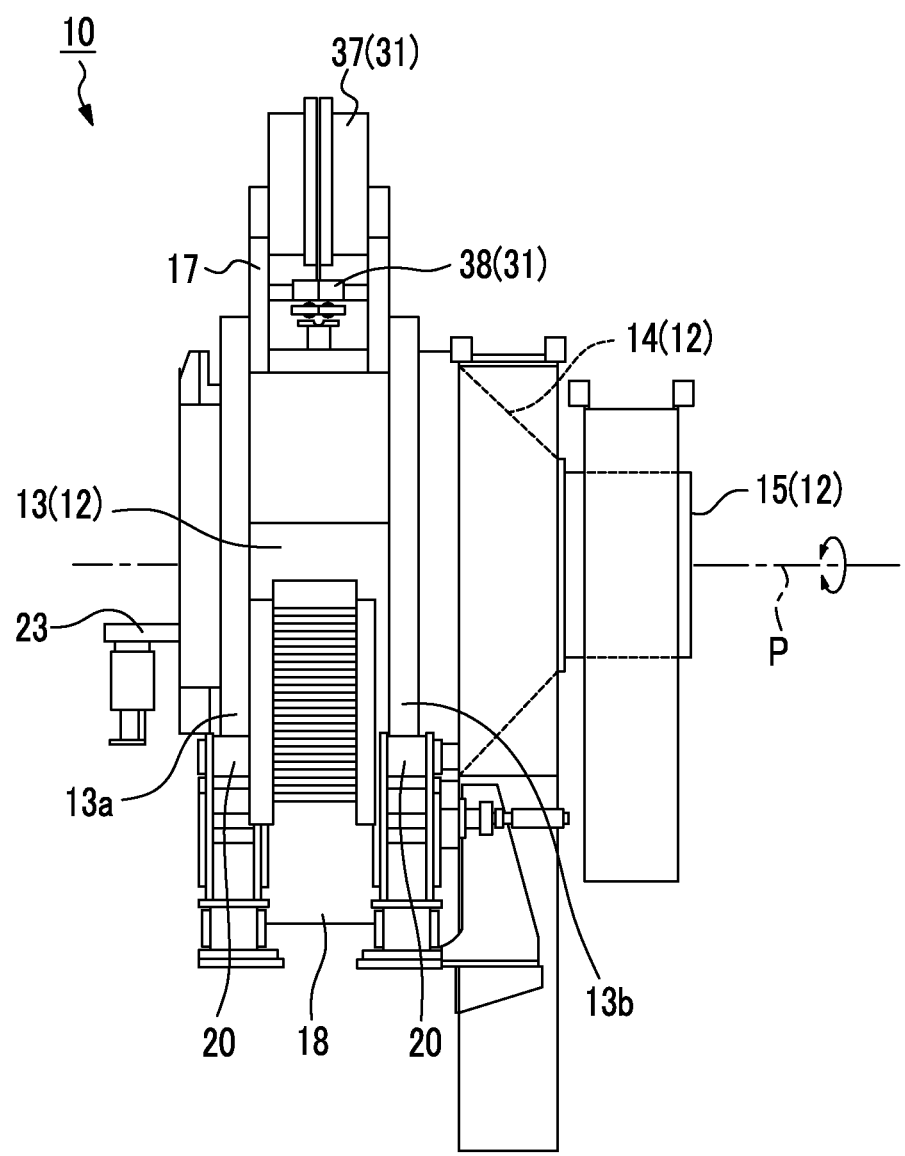
FIG. 5 is a left side view of the proton beam therapy apparatus according to the embodiment of the present invention.
Figure 6:
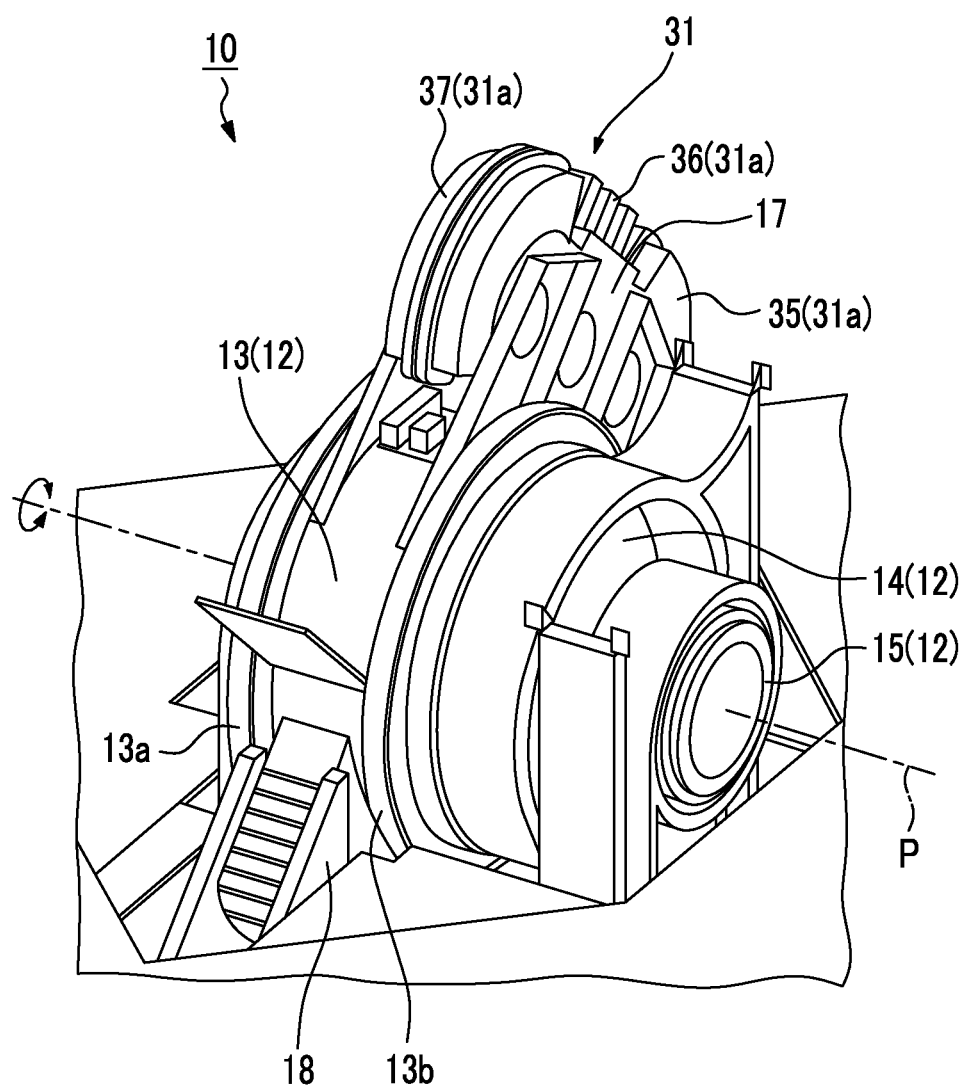
FIG. 6 is a perspective view showing the proton beam therapy apparatus according to the embodiment of the present invention from the oblique rear.

In the proton beam therapy apparatus 10, a portion of the beam introduction line 31 which transports the proton beam B is formed so as to pass through the insides of the second cylindrical section 15, the cone section 14, and the cylindrical main body section 13 of the rotating gantry 12. In particular, the inclined section 33 of the beam introduction line 31 is obliquely disposed so as to pass through the inside of the irradiation chamber 21 (the cylindrical main body section 13), and thus the beam introduction line 31 led in from the back side of the rotating gantry 12 can be led out from a side portion of the rotating gantry 12. For this reason, compared to a case where the beam transport line is formed to avoid the irradiation chamber 21, it is possible to reduce the amount of overhanging (the maximum outer diameter from an axis center) of a beam line. In this way, it is possible to attain a reduction in the size of the proton beam therapy apparatus 10 and thus reduce an installation space in which the proton beam therapy apparatus 10 is installed. As a result, a reduction in the size of the building 5 which accommodates the proton beam therapy apparatus 10 can be attained. By reducing the size of the building, it is possible to reduce the amount of concrete which is used for, for example, a radiation shield wall of the building, and therefore, it is possible to reduce the construction cost of the building. In addition, as shown in FIG. 2, the maximum rotation outer diameter of the proton beam therapy apparatus 10 can be set to be 10.6 m ($L_1 \times 2$).

Furthermore, in the proton beam therapy apparatus 10, since a portion (the inclined section) of the beam introduction line 31 is obliquely disposed so as to pass through the back panel and the inside of the irradiation chamber 21, as compared with a case where the beam introduction line 31 is disposed so as to avoid the irradiation chamber 21, it is possible to shorten the length of the beam introduction line which is disposed on the back side of the irradiation chamber 21. That is, in the proton beam therapy apparatus 10, the entire apparatus is reduced in size also in the direction of the rotation axis P.

Furthermore, in the proton beam therapy apparatus 10 according to this embodiment, the beam introduction line (the beam transport line) 31 is supported by the cylindrical main body section (the tubular body) 13 of the rotating gantry 12. In this way, a plurality of electromagnets that are optical elements configuring the beam introduction line 31 is supported by the cylindrical main body section 13 that functions as a strength member, and thus the weight of the electromagnets can be received by the cylindrical main body section 13, and therefore, it is possible to suitably disperse a force acting on the cylindrical main body section 13. Furthermore, since the back panel 16 is provided on one end side of the cylindrical main body section 13, it is possible to make the back panel 16 function as a strength member.

The present invention has been specifically described above on the basis of embodiments thereof. However, the present invention is not limited to the above-described embodiments. For example, each element configuring the beam introduction line 31 can be appropriately changed in disposition or the number thereof according to a desired beam design.

Furthermore, the particle accelerator is not limited to a cyclotron but may be a synchrotron or a synchro-cyclotron. Furthermore, the charged particle beam is not limited to a proton beam but may be a carbon beam (a heavy particle beam). Furthermore, the tubular body of the rotating gantry 12 is not limited to a cylinder but may have another tubular shape. Furthermore, the tubular body of the rotating gantry 12 may have the same shape in the direction of the rotation axis P.

The rotating gantry 12 is not limited to a configuration in which it rotates (oscillates) 360°, but a configuration in which oscillation of less than 360° is performed may also be used.

Furthermore, a configuration in which a cutout portion is provided in a portion, for example, a side wall of the tubular body may also be used. In addition, since a configuration in which the beam introduction line 31 is disposed so as to pass through the tubular body is used, a configuration in which the beam introduction line 31 is disposed in the cutout portion provided in the tubular body may be used.

Furthermore, a configuration in which a cutout portion is provided in the back panel may be used. In addition, a configuration in which the beam introduction line 31 is disposed so as to pass through the back panel also includes a configuration in which the beam introduction line 31 is disposed in the cutout portion provided in the back panel. It is acceptable if the beam introduction line 31 is disposed so as to pass through a cutout portion or an opening portion provided in the back panel.

Furthermore, in the above-described embodiments, the inclined section is formed in a linear shape. However, for example, an inclined section which is curved gently may also be used.

A beam introduction line support section which supports the beam introduction line 31 is not limited to the configuration described above, but other configurations may also be used. The beam introduction line support section may have, for example, a configuration in which the first support member 51, the second support member 52, and the third support member 53 are connected and integrated with each other. Furthermore, the beam introduction line support section may have a configuration in which the beam introduction line 31 is supported by the first support member 51 and the third support member 53 without using the second support member 52. Furthermore, the first support member 51 may have a configuration in which it is fixed to the cone section 14. The beam introduction line support section may have a configuration in which support members are disposed on both sides with the beam introduction line 31 interposed therebetween.

The disposition of the quadrupole electromagnet 41, the steering electromagnet 42, and the profile monitor 43 is not limited to that which is described in the above-described embodiments but can be appropriately changed. Furthermore, it is not limited to a configuration having the quadrupole electromagnet 41, the steering electromagnet 42, and the profile monitor 43, but a charged particle beam irradiation apparatus which is not provided with one of them may also be used.

The charged particle beam irradiation apparatus is not limited to a configuration in which a portion (the inclined section) of the beam introduction line 31 passes through the back panel 16 and the inside of the irradiation chamber 21. For example, in a case where a sufficient space for passage of the beam introduction line 31 is present between the irradiation chamber 21 and the cylindrical main body section 13 and the cone section 14, a charged particle beam irradiation apparatus may also be used in which the beam introduction line 31 is disposed between the irradiation chamber 21 and the cylindrical main body section 13 and the cone section 14.

In the charged particle beam irradiation apparatus according to an embodiment of the present invention, since a reduction in size is attained, an apparatus accommodation space is reduced, and thus it is possible to attain a reduction in the size of a building in which the charged particle beam irradiation apparatus is installed. The charged particle beam irradiation apparatus according to an embodiment of the present invention is effective for a reduction in the construction cost of the building.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus comprising:
    a transport line configured to transport a charged particle beam; and
    a rotating gantry rotatable around a rotation axis,
    wherein the transport line comprises
        an inclined section configured to make the charged particle beam advancing in a direction of the rotation axis advance to be inclined so as to become more distant from the rotation axis,
        a rotation section configured to turn the charged particle beam advanced in the inclined section to a rotational direction of the rotation axis; and
        a bending section configured to bend the charged particle beam turned to the rotational direction to the rotation axis,
    the rotating gantry is formed of a tubular body which accommodates an irradiated body and supports the transport line, and
    the inclined section of the transport line is disposed to pass through the inside of the tubular body of the rotating gantry,
    wherein the rotating gantry has an irradiation chamber in which one end side in a direction in which the rotation axis extends is closed by a back panel, and
    the inclined section of the transport line is disposed to pass through the back panel and the inside of the tubular body of the rotating gantry.

2. The charged particle beam irradiation apparatus according to claim 1, wherein the transport line includes
    a first bent section configured to change a traveling direction of the charged particle beam advancing in the direction of the rotation axis and introduce the charged particle beam into the inclined section,
    a second bent section that is provided downstream of the inclined section and configured to change the traveling direction of the charged particle beam to a direction orthogonal to the rotation axis,
    a third bent section that is provided downstream of the second bent section and configured to change the traveling direction of the charged particle beam to the rotational direction of the rotation axis, and
    a fourth bent section configured to bend the charged particle beam passed through the inside of the third bent section to the rotation axis side.

3. A charged particle beam irradiation apparatus comprising:
    a transport line configured to transport a charged particle beam; and
    a rotating gantry rotatable around a rotation axis,
    wherein the transport line has at least an inclined section configured to make the charged particle beam advancing in a direction of the rotation axis advance to be inclined so as to become more distant from the rotation axis,
    the rotating gantry has an irradiation chamber of a tubular body in which one end side in a direction in which the rotation axis extends is closed by a back panel, and
    the inclined section of the transport line is disposed to pass through the back panel and the inside of the tubular body of the rotating gantry.

\* \* \* \* \*